United States Patent [19]

Herrera

[11] Patent Number: 4,469,095
[45] Date of Patent: Sep. 4, 1984

[54] MEDICAL SLEEVE
[76] Inventor: Olivia H. Herrera, P.O. Box 1312, Pueblo West, Colo. 81002
[21] Appl. No.: 438,025
[22] Filed: Dec. 28, 1982
[51] Int. Cl.³ .............................................. A61F 13/00
[52] U.S. Cl. ...................................................... 128/65
[58] Field of Search .............. 128/165, 157, 155, 156, 128/77

[56] References Cited
U.S. PATENT DOCUMENTS
3,000,378 9/1961 Zieman ................................ 128/165
3,975,929 8/1976 Fregeolle ............................ 128/165
4,172,456 10/1979 Zens .................................... 128/165

Primary Examiner—Stephen C. Pellegrino
Attorney, Agent, or Firm—John Cyril Malloy

[57] ABSTRACT

A medical sleeve wherein a knitted sleeve length is provided to extend from a snug location of the lower end adjacent the wrist of a wearer all along the entire length of an arm to the shoulder and wherein a strap is provided for hooked-up engagement through snap means to connect the sleeve to a brazier strap, which device is useful after a masectomy.

6 Claims, 5 Drawing Figures

FIG. 4 is a view similar to FIG. 3 and in cross section;
FIG. 5 is an enlarged view illustrating the attachment of the device to the brazier of a wearer.

DESCRIPTION OF THE PREFERRED EMBODIMENT

Referring to the drawings wherein like reference characters designate like or corresponding parts throughout the several views and referring particularly to FIG. 1, the medical sleeve is generally designated by the numeral 11 and it is adapted to be attached to the strap 21 of a brazier worn by a wearer. To the upper end of the sleeve there is provided an elastic band for hooked-up engagement underneath the brazier strap 21, the band being designated by the numeral 19.

Referring more particularly to FIG. 2, it is seen that the sleeve has a lower end 13 which is preferably of double knit structure and this provides a lower end to snugly jacket the wrist of a wearer. The entire length of the sleeve 11 is of knit material, such as is often used in stockings and which is of the type described, for example, in U.S. Pat. No. 3,975,929 dated Aug. 24, 1976 for a Thigh Length Anti-Embolism Stocking And Method Of Knitting The Same, issued to Oscar Fregeolle. At the upper end zone 15 the number of stitches is reduced somewhat so that the side opening which accommodates the arm of a wearer, see FIG. 4, faces in the direction of the armpit and the reduced number of stitches are indicated in the zone 17. About the margin of the opening at the top and at the upper side of this opening, there extends the elastic band 19 which is connected to the sleeve at the margin of the upper opening by mutually intercooperating means, such as the snap 25 on the sleeve and the socket 23 on the distal end of the band 19.

It is thus seen that there has been provided an extremely comfortable useful type of medical sleeve.

Figure 1:
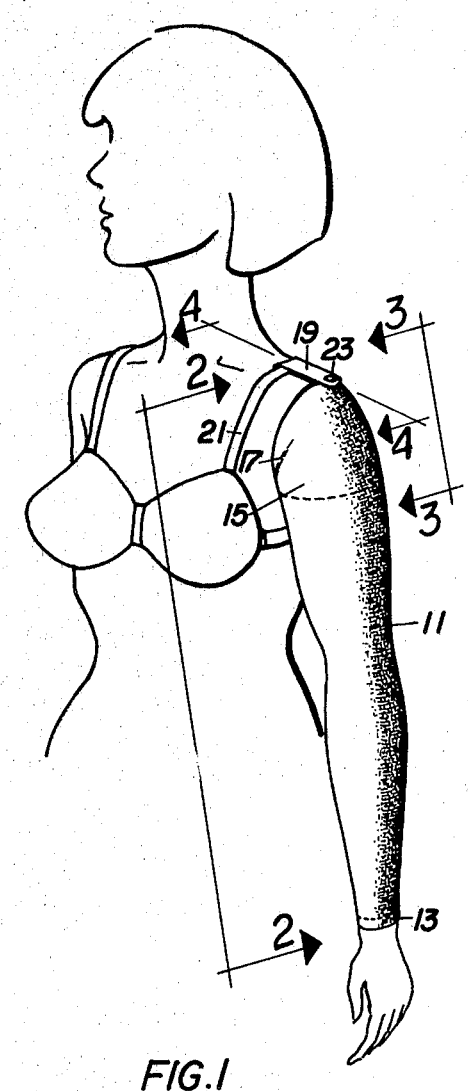
FIG. 1 is a perspective view illustrating the instant invention.
Figure 2:
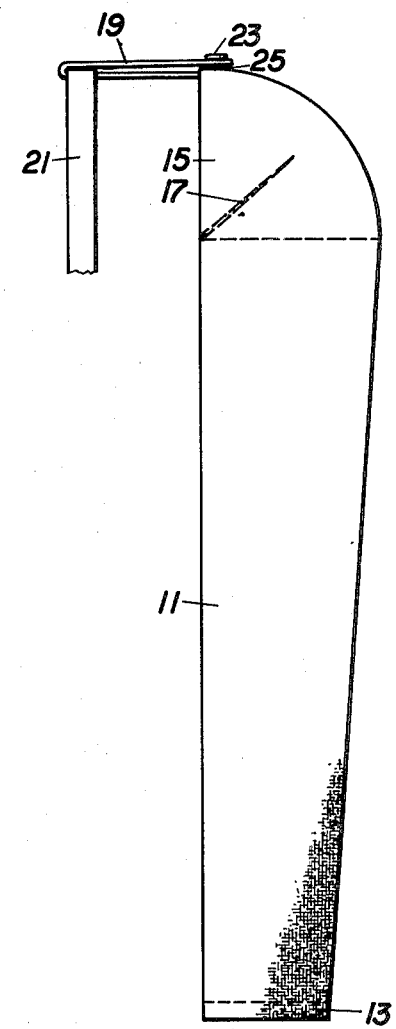
FIG. 2 is a view of the medical sleeve as indicated by the arrowed line 2—2 in FIG. 1.
Figure 3:
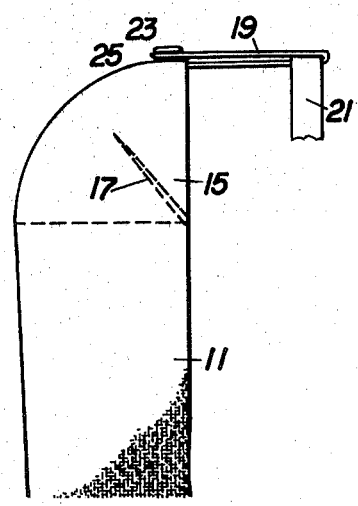
FIG. 3 is a view of the upper portion of FIG. 1.
Figure 4:
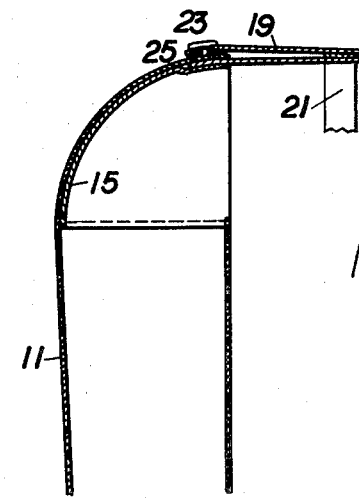
Figure 5:
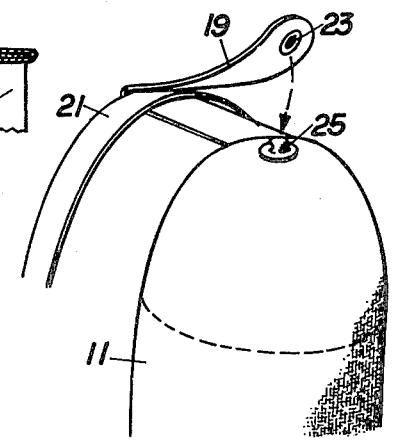

What is claimed is:

1. A medical sleeve adapted to jacket either arm of a user comprising:
   an integral elongated tubular seamless length having an upper portion, a lower portion, and a cap portion;
   said tubular length fabricated of continuous woven elastic knitted material and adapted to fit snugly over the user's entire arm;
   said cap portion adjacent the upper end of said upper portion;
   said lower portion adjacent the lower end of said upper portion and having a wrist portion;
   said cap portion forming said sleeve upper opening, said upper opening generally perpendicular and offset from the overall axis of said tubular length and adapted to receive and snugly fit over the user's shoulder and armpit;
   a length of elastic band connected at one end to the upper portion of said cap portion; and
   intercooperating fastening means on the distal end of said band and said upper portion of said cap portion adapted for releasable engagement of said band about the brazier strap of the user to maintain positioning of said sleeve on the user's arm;
   said wrist portion forming said lower axial opening of said sleeve;
   said wrist portion adapted to snugly jacket the user's wrist to maintain the position of said lower portion along the user's arm.
2. A medical sleeve as set forth in claim 1, wherein: said tubular length is one-ply support type elastic nylon.
3. A medical sleeve as set forth in claim 1, wherein: said tubular length is cotton-blend.
4. A medical sleeve as set forth in claim 1, wherein: said wrist portion is double edged and sewn.
5. A medical sleeve as set forth in claim 1, wherein: said medical sleeve is flesh color.
6. A medical sleeve as set forth in claim 1, wherein: said cap portion is shaped by a decreasing number of stitches along the front and rear portions of said cap portion.

* * * * *

MEDICAL SLEEVE

FIELD OF THE INVENTION

This invention relates to a medical sleeve and to a sleeve which is sometimes known as a lymphodema sleeve.

BACKGROUND OF THE INVENTION

In the past there have been numerous types of limb encircling devices, such as that of U.S. Pat. No. 3,279,459 and U.S. Pat. No. 3,000,378. These devices are designed to provide some compression to a limb of a person. A similar tubular body support is taught in U.S. Pat. No. 4,084,586. Also, a Surgical Stocking is described in U.S. Pat. No. 1,287,870 for a leg or optionally the elbow zone or wrist zone of a body. It has been determined that an elastic support for a body extremity is helpful in many situations, see U.S. Pat. No. 4,166,463. Also, in the past, there have been numerous types of thigh length stockings, such as the Anti-Embolism Stocking And Method Of Knitting Same, described in U.S. Pat. No. 3,975,929.

SUMMARY OF THE PRESENT INVENTION

The present invention is of a medical sleeve of a material such as that described in U.S. Pat. No. 3,975,929 and which sleeve is for use on the arm of a wearer to jacket the entire length thereof. It will be appreciated that following a radical masectomy swelling of the arm always results as well as a severe sensitivity underneath the arm. This discomfort has been the subject of numerous efforts to alleviate it and numerous apparatuses including very tight fitting bandages have been suggested; however, these tend to cutoff circulation and must be taken off every several hours.

This invention is of an elastic sleeve, such as a one-ply support type elastic nylon stocking, preferably of a cotton blend, which fits over the arm comfortably fitting the wearer and can be worn for substantial periods of time, indefinitely. The sleeve has an upper and lower portion, the lower portion is double edge and sewn in order to fit comfortably yet snugly around the wrist without rolling and the upper portion is provided with a band over the armpit or top of the shoulder of a length to reach to the brazier strap. It is held by a simple snap which holds the sleeve in place at the shoulder. The present invention being of the material described does not require the assistance of another person in order to put it on. The person simply inserts her arm into the sleeve and adjusts it. There is a reduction in the bulk of the prior art devices and it can be washed relatively easy, in a manner resembling conventional stockings, without losing its shape. In the preferred embodiment, there will be three sizes, small, medium and large. In any event, the device provides for increased feelings of comfort and use by a person following such an operation as that described. In the preferred embodiment, the device is flesh colored so that one does not find that it is a stark looking device so that it can be worn conveniently under blouses.

OBJECTS OF THE INVENTION

The medical sleeve of the instant invention has many advantages over the various types that are now in existence. It controls the swelling of the entire arm including the hand and fingers which is caused by excess fluids without interferring with the normal blood circulation. Because of the shearness and fact that it is very comfortable to the wearer, it does not produce heat or perspiring and is easy to put on with a one hand operation without requiring assistance of another. It does not have to be removed periodically to relieve excess pressure or to improve circulation. There are no seams to irritate the wearer and it is thin enough to be worn under regular clothing. It will not "ride up" during activities and can be made of normal skin tones as are the stockings which are currently on the market. It is of tremendous help phsychologically to persons who have had such an operation as that known as a masectomy. The upper portion is held in position with the aid of short elastic tab with a snap-type fastener means, the tab being adapted to connect to a brazier strap to hold the sleeve in position. The snap is attached to the end of the elastic band for connection to a cooperating snap means on the upper zone of the sleeve. The tab is passed under the brazier strap and doubled over and attached to itself. This has been found to be sufficient to maintain the position of the sleeve during substantially all activities.

Because of the shearness, the sleeve can be washed in the same way as conventional stockings and hung up to dry overnight. Washing does not alter the shape or tension of the device. The sleeve can be used on either the right or the left arm and the sleeve can be produced at a much lower cost than the existing medical sleeve in three sizes, small, medium and large. The upper end of the sleeve, in a preferred embodiment, is made of soft elastic cotton knit for comfort and for absorption of normal underarm perspiration. The entire sleeve minus the tab can be knit in one continuous operation with the cap portions being shaped by a decreasing number of stitches in the front and rear portion of the underarm section as shown in the attached drawings in the same manner as the heel of a conventional stocking is shaped. The tab in the preferred embodiment is one-half inches wide and about four inches long and preferably is of a white elastic band material. One inch of the tab is sewn into the inside of the upper end of the arm and the male half of the snap is attached to the center outside surface of the cap. The female position is preferably attached one-half inch from the other end of the tab on the upper side of the tab. The wrist portion is preferably of double knit for the first one-half inches to eliminate "ride up" and to snugly jacket the arm. The main portion of the sleeve may be of knit material such as 82% nylon, 18% elastane, the cap being of 82% cotton and 18% elastane. In any event, cotton material is preferred in the upper zone of the arm at the armpit of a wearer. A stitch commonly used in support stockings is preferred.

As an overall object, it is seen that there is provided a medical sleeve which is comfortable, easily washed, fits snugly along the arm of a user, is seamless, and is not bulky.

It is accordingly an object of this invention to provide an improved medical sleeve which is simple and inexpensive to manufacture, comfortable in use, washable, and which provides a reduction in the discomfort heretofore experienced by users of such devices.